United States Patent [19]

Takahashi

[11] Patent Number: 5,083,020
[45] Date of Patent: Jan. 21, 1992

[54] MASS SPECTROMETER

[75] Inventor: Sadao Takahashi, Katsuta, Japan

[73] Assignee: Hitachi, Ltd., Tokyo, Japan

[21] Appl. No.: 53,368

[22] PCT Filed: Aug. 27, 1986

[86] PCT No.: PCT/JP86/00439
§ 371 Date: Apr. 30, 1987
§ 102(e) Date: Apr. 30, 1987

[87] PCT Pub. No.: WO87/01452
PCT Pub. Date: Mar. 12, 1987

[30] Foreign Application Priority Data

Aug. 29, 1985 [JP] Japan ................................. 60-190377

[51] Int. Cl.$^5$ ............................................. H01V 49/04
[52] U.S. Cl. ..................................... 250/288; 250/309
[58] Field of Search ............................... 250/288, 309

[56] References Cited

FOREIGN PATENT DOCUMENTS 48-7089   1/1973 Japan .
51-111482 10/1976 Japan .
53-116787  9/1978 Japan ................... 250/309
57-161540 10/1982 Japan .

Primary Examiner—Jack I. Berman
Attorney, Agent, or Firm—Antonelli, Terry, Stout & Kraus

[57] ABSTRACT

An apparatus for analyzing masses of ions that are produced when sample components carried on a target 6 are bombarded with a primary beam 4. Production of ions and neutral particles from portions other than sample components A to D on the target 6 should to be minimized as much as possible. To fulfill this assignment, the primary beam 4 is prevented from bombarding the target 6 when portions between the sample components A to D on the target 6 pass the position where they will be bombarded with the primary beam.

4 Claims, 1 Drawing Sheet

FIG. 1
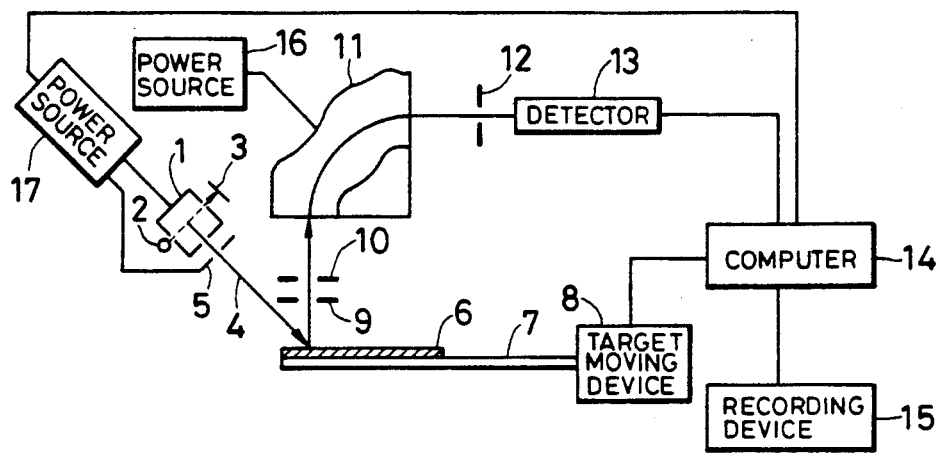
FIG. 2
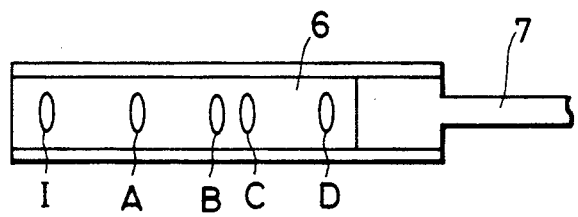
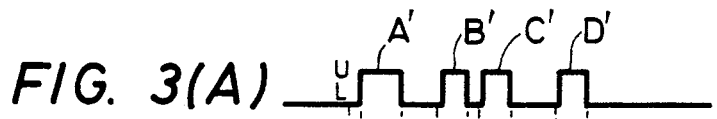
FIG. 3(A)
FIG. 3(B)
FIG. 4
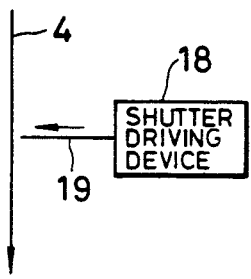
FIG. 5
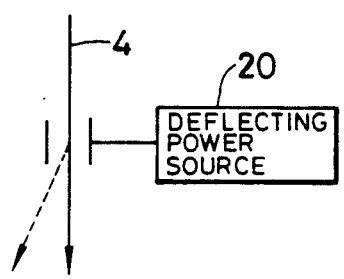

MASS SPECTROMETER

TECHNICAL FIELD

The present invention relates to a mass spectrometer, and more particularly to a mass spectrometer adapted to analyzing masses of sample components held by a target such as a thin layer chromatography plate (hereinafter referred to as TLC plate).

BACKGROUND ART

Study has been forwarded in recent years concerning a TLC/SIMS method to analyze sample components held by a TLC plate relying upon a secondary ion mass spectroscopy (SIMS). This method can easily analyze a sparringly volatile mixture without using liquid chromatography, and hence is expected to come into general use in the future.

According to the thin layer chromatography, the plate is made up of a substrate such as of aluminum and an adsorption layer such as of silica gel formed on the surface of the substrate. A mixture sample is added to an end of the plate, and the end is dipped in a developing solvent, whereby the mixture is developed with the developing solvent and is separated into individual components.

The plate which carries the thus separated sample components is set to a predetermined position in the mass spectrometer, and is so moved that the sample components carried on the surface thereof successively pass through a position where they are bombarded with a primary beam.

Upon bombardment with the primary beam such as ion beam, the sample components are sputtered, and ions formed by the sputtering are subjected to mass dispersion due to the magnetic field. Among the ions, only those ions having a particular mass number are detected by a detector. Further, the intensity of the magnetic field or the ion acceleration voltage is swept, to successively detect ions having various mass numbers.

As the sample components are sputtered by the primary beam, generation of ions therefrom decreases gradually. In order to prevent this phenomenon, a matrix such as glycerol is applied onto the surface of the plate prior to setting the plate to a predetermined position in the mass spectrometer. The sample components are partly made lower as they are sputtered by the primary beam. Here, the matrix promotes the migration of the surrounding sample components into the reduced portion, so that generation of ions is prevented from decreasing.

According to the above-mentioned method, the TLC plate is continuously moved, and the primary beam keeps falling on the target at all times. Therefore, the primary beam falls even on those portions other than the sample components on the target, whereby undesired neutrons and ions are produced by the matrix on the portions other than the sample components. These particles contaminate the parts such as slits to deteriorate the performance of mass spectrometry.

DISCLOSURE OF INVENTION

An object of the present invention is to provide a mass spectrometer which is adapted to reducing the generation of ions and neutrons from the portions other than the sample components carried by a target such as a TLC plate.

Another object of the present invention is to provide a mass spectrometer which is adapted to alleviate the trouble of contamination caused by ions and neutrons generated from the portions other than the sample components carried by a target such as a TLC plate.

According to the present invention, there is provided a mass spectrometer which comprises: means for generating a primary beam so that a first predetermined position is irradiated with the primary beam; means for holding a target which carries sample components; means for moving said target so that each of the sample components is moved to said first predetermined position; means for subjecting ions to mass dispersion, the ions being produced when the sample components are sputtered by said primary beam at said first predetermined position; means for effecting mass number sweeping so that ions that are subjected to the mass dispersion and that have various mass numbers pass a second predetermined position; means for detecting ions which have passed said second predetermined position; and means for interrupting said primary beam from bombarding said target when portions among the sample components on said target pass said first predetermined position.

BRIEF DESCRIPTION OF DRAWINGS

FIG. 1 is a block diagram of a mass spectrometer according to an embodiment of the present invention;

FIG. 2 is a top view showing a target and a target holder of FIG. 1;

FIG. 3(A) is a diagram of waveforms for controlling the movement of the target;

FIG. 3(B) is a diagram of waveforms for controlling the primary beam acceleration voltage and for controlling the lens electrode voltage;

FIG. 4 is a schematic diagram of means for interrupting the primary beam directed to the target according to another embodiment; and FIG. 5 is a schematic diagram of means of interrupting the primary beam directed to the target according to a further embodiment.

BEST MODE FOR CARRYING OUT THE INVENTION

Referring to FIG. 1, an inert gas such as xenon gas is introduced into an ionization chamber 1 and is ionized being bombarded with electrons that are emitted from a filament 2 toward a collector 3. The ions which are generated are accelerated by an acceleration voltage of about 8 to 10 kV that is applied to the ionization chamber 1, and are emitted as an ion beam 4 out of the ionization chamber 1. The ion beam which serves as a primary beam is focused by a lens electrode 5 on a target 6.

The target 6 consists of a TLC plate. Namely, the target 6 includes a substrate such as of aluminum and an adsorption layer such as of silica gel formed on the surface thereof. Sample components developed and separated by the TLC are adsorbed and carried by the adsorption layer, and a matrix such as glycerol is applied onto the surface of the adsorption layer.

The target 6 is held by a target holder 7 which is supported by a target moving device 8. The sample components on the target 6 are moved by the target moving device 8 to a position where they are bombarded with the ion beam and are sputtered by the ion beam 4 so that secondary ions are generated. An acceleration voltage of about 3 kV has been applied to the target 6. Therefore, the energy of ion beam 4 that impinges upon the target 6 is 5 to 7 keV, and the energy which accelerates the secondary ions is 3 keV.

The accelerated secondary ions pass through a lens slit 9 and a source slit 10, and are separated depending upon their mass numbers by a magnetic field generated by a magnet 11. Namely, mass-dispersion is effected. Among the ions that are mass-dispersed, the ions of a particular mass number that pass through a collector slit 12 are detected by a detector 13.

Signals from the detector 13 are all stored in a computer 14 which produces a chromatogram signal by total ions, a chromatogram signal by ions of a particular mass number, and a mass spectrum signal, according to the data stored therein. The output signals are recorded in a recording device 15.

FIG. 2 is a top view of the TLC plate which is the target of FIG. 1. In FIG. 2, symbol I denotes a position where a mixture sample will be added, and symbols A to D denote sample components that are developed and separated by means of the TLC. Usually, the portions I and A to D are colored so that they can be distinguished from other portions with the naked eye. When the portion I is regarded to be a reference position, therefore, the positions A to D can be easily measured using a rule. When the portion I is regarded to be a reference position, the measured positions A to D and sizes of the sample components A to D in a direction in which the TLC plate 6 moves, are stored in the computer 14. Based upon the stored positions and dimensional data, the computer 14 so controls the target moving device 8 that the TLC plate 6 is moved slowly when the sample components A to D on the TLC plate 6 passes the position where they will be bombarded with the ions and that the TLC plate 6 is moved at a high speed in other moments, i.e., the TLC plate 6 is moved at a high speed when portions among the sample components A to D pass the position where the components will be bombarded by the ions. The computer 14 further so controls the magnetic field power source 16 that a mass number of ions is swept while the TLC plate 6 is moving slowly. The mass number of ions may be swept only one time or a plurality of times while the TLC plate 6 is slowly moving. In the latter case, the computer 14 integrates and averages the signals of the detector 13 obtained through a plurality times of mass number sweepings every time when the TLC plate 6 has moved slowly, i.e., every time when each of the sample components A to D has passed the position of ion bombardment; the computer 14 produces the averaged data.

FIG. 3(A) shows waveforms for controlling the movement of the TLC plate 6, wherein the abscissa represents the time. The TLC plate 6 moved slowly during the period of an upper level U and moves at a high speed during the period of a lower level L. Symbols A' to D' correspond to A to D of FIG. 2. Therefore, the TLC plate 6 moves slowly when the sample components A to D pass the position where they will be bombarded with the ions. The sample components A to D seldom have the same size in the direction in which the TLC plate 6 moves. This is why the waveforms A' to D' have dissimilar widths.

FIG. 3(B) shows waveforms for controlling the acceleration voltage and the lens electrode voltage that are applied to the ionization chamber 1 and the lens electrode 5, and wherein the abscissa represents the time. The acceleration voltage and the lens electrode voltage are on during the period of the upper level U and are off during the period of the lower level L. As will be obvious, the acceleration voltage and the lens electrode voltage are turned off at the time when the moving speed of the TLC plate 6 is changed from a low speed to a high speed. Here, the moment when these voltages are turned on is earlier than the moment at which the moving speed of the TLC plate 6 is changed from the high speed to the low speed. This is because by the moment when the TLC plate 6 is switched from the high-speed movement to the low-speed movement, the acceleration voltage and the lens electrode voltage are desired to have been returned to normal values.

The computer 14 produces control signals shown in FIG. 3(B) based upon the data stored therein, and the control signals are supplied to the power source 17, which applies the acceleration voltage and the lens electrode voltage to the ionization chamber 1 and the lens electrode 5, respectively. As the control signals shown in FIG. 3(B) are supplied to the power source 17, therefore, the acceleration voltage and the lens electrode voltage applied to the ionization chamber 1 and the lens electrode 5 are controlled, i.e., turned on and off according to the waveforms shown in FIG. 3(B).

When the acceleration voltage and the lens electrode voltage are turned off, no ion beam 4 is emitted from the ionization chamber 1, and the bombardment of ion beam 4 upon the TLC plate 6 is avoided. Here, the acceleration voltage and the lens electrode voltage are turned off at the moments when the portions among the sample components A to D pass the position of ion beam bombardment. At these moments, therefore, undesired neutrons and secondary ions are not generated from the TLC plate 6, and the parts such as slits 9 and 10 are prevented from being contaminated by such particles. Therefore, the performance of the mass spectrometry is prevented from being deteriorated due to the contamination.

In order that the TLC plate 6 is not bombarded by the ion beam 4 when the portions among the sample components A to D pass the position of ion beam bombardment, a shutter 19 may be inserted in a path of ion beam 4 by a shutter drive device 18 shown in FIG. 4, or a deflector 21 may be energized by a deflecting power source 20 to deflect the ion beam 4 as indicated by a dotted line in FIG. 5, in addition to turning off the acceleration voltage as was described earlier.

When the sample components A to D have moved to the position where they will be bombarded with the ion beams, the TLC plate may be brought into halt completely instead of being moved slowly as was described earlier.

Instead of bombarding the TLC plate 6 with the ion beam 4, means for converting the ion beam 4 into a neutral beam may be provided between the lens electrode 5 and the TLC plate 6, so that the TLC plate 6 is bombarded with the thus converted neutral beam.

In connection with the above-mentioned details, it should be noted that the present invention can be changed or modified in a variety of other ways without departing from the spirit and scope of the invention, and that the invention is in no way limited to the aforementioned embodiments only.

What is claimed is:
1. A mass spectrometer comprising:
means for generating a primary beam;
means for applying an acceleration voltage which accelerates said primary beam so that the acceler- ated primary beam is directed toward a first predetermined position;

means for holding a target which carries sample components;

means for moving said target so that each of the sample component is moved in seriatim to said first predetermined position, said moving means so controlling the movement of said target that said sample components pass said first predetermined position at a first predetermined speed, and that the portions other than said sample components on the target pass said first predetermined position at a second predetermined speed which is faster than said first predetermined speed;

means for subjecting ions to mass dispersion, the ions being produced when the sample components are bombarded by said primary beam at said first predetermined position;

means for effecting mass number sweeping so that ions that are subjected to the mass dispersion and have various mass numbers pass a second predetermined position;

means for detecting ions which have passed said second predetermined position; and means for interrupting said primary beam to prevent said primary beam from bombarding portions between adjacent sample components on said target when said portions pass said first predetermined position.

2. A mass spectrometer according to claim 1, wherein said means for interrupting said primary means from bombarding said target includes means which interrupts the application of said acceleration voltage.

3. A mass spectrometer according to claim 2, wherein said means for interrupting said primary beam from bombarding said target includes a shutter that cuts off said primary beam.

4. A mass spectrometer according to claim 2, wherein said means for interrupting said primary beam from bombarding said target includes means which deflects said primary beam.

* * * * *